US009072558B2

(12) United States Patent
Orbay

(10) Patent No.: US 9,072,558 B2
(45) Date of Patent: *Jul. 7, 2015

(54) DISTAL RADIUS FRACTURE FIXATION PLATE WITH ULNAR BUTTRESS

(71) Applicant: Biomet C.V., Gibraltar (GI)

(72) Inventor: Jorge L. Orbay, Coral Gables, FL (US)

(73) Assignee: BIOMET C.V., Gibraltar (GI)

( * ) Notice: Subject to any disclaimer, the term of this patent is extended or adjusted under 35 U.S.C. 154(b) by 0 days.

This patent is subject to a terminal disclaimer.

(21) Appl. No.: 13/966,391

(22) Filed: Aug. 14, 2013

(65) Prior Publication Data

US 2014/0058456 A1    Feb. 27, 2014

Related U.S. Application Data

(63) Continuation of application No. 12/791,405, filed on Jun. 1, 2010, now Pat. No. 8,556,945, which is a continuation of application No. 10/664,371, filed on Sep. 17, 2003, now Pat. No. 7,857,838.

(51) Int. Cl.
*A61B 17/80*    (2006.01)
*A61B 17/86*    (2006.01)
*A61B 17/56*    (2006.01)

(52) U.S. Cl.
CPC ........... *A61B 17/809* (2013.01); *A61B 17/8057* (2013.01); *A61B 17/8061* (2013.01); *A61B 17/863* (2013.01); *A61B 2017/565* (2013.01); *A61B 17/8095* (2013.01)

(58) Field of Classification Search
CPC .... A61B 17/58; A61B 17/7059; A61B 17/80; A61B 17/8052; A61B 17/8057; A61B 17/8061

USPC ......... 606/280, 283, 284, 286, 287, 291, 298, 606/299

See application file for complete search history.

(56) References Cited

U.S. PATENT DOCUMENTS

| | | | |
|---|---|---|---|
| 388,000 | A | 8/1888 | Rider |
| 472,913 | A | 4/1892 | Taylor |
| 1,151,861 | A | 8/1915 | Brumback |
| 2,056,688 | A | 10/1936 | Peterka et al. |
| 2,500,370 | A | 3/1950 | McKibbin |
| 2,526,959 | A | 10/1950 | Lorenzo |
| 3,025,853 | A | 3/1962 | Mason |

(Continued)

FOREIGN PATENT DOCUMENTS

| | | |
|---|---|---|
| CA | 2174293 A | 10/1997 |
| CH | 675 531 | 10/1990 |

(Continued)

OTHER PUBLICATIONS 3.5 mm LCP Anterolateral Distal Tibia Plates, Technique Guide, Synthes, 2006.

(Continued)

*Primary Examiner* — Anu Ramana
(74) *Attorney, Agent, or Firm* — Gordon & Jacobson, PC

(57) ABSTRACT

A distal volar fixation plate includes a body portion and a head portion angled upwards relative to the body portion. The head portion includes a lower surface, a central portion, a radial side and an ulnar side. The head portion defines a buttress portion extends greater distally on the ulnar side than on the radial side to support the volar lip of the lunate fossa.

18 Claims, 6 Drawing Sheets

(56) References Cited

U.S. PATENT DOCUMENTS

| | | |
|---|---|---|
| 3,236,141 A | 2/1966 | Smith |
| 3,561,437 A | 2/1971 | Orlich |
| 3,645,161 A | 2/1972 | Wesker |
| 3,707,107 A | 12/1972 | Bieri |
| 3,709,218 A | 1/1973 | Halloran |
| 3,717,146 A | 2/1973 | Halloran |
| 3,741,205 A | 6/1973 | Markolf et al. |
| 3,842,825 A | 10/1974 | Wagner |
| 3,939,498 A | 2/1976 | Lee et al. |
| RE28,841 E | 6/1976 | Allgower et al. |
| 4,011,863 A | 3/1977 | Zickel |
| 4,119,092 A | 10/1978 | Gil |
| 4,135,507 A | 1/1979 | Harris |
| 4,153,953 A | 5/1979 | Grobbelaar |
| 4,169,470 A | 10/1979 | Ender et al. |
| 4,172,452 A | 10/1979 | Forte et al. |
| 4,408,601 A | 10/1983 | Wenk |
| 4,467,793 A | 8/1984 | Ender |
| 4,473,069 A | 9/1984 | Kolmert |
| 4,483,335 A | 11/1984 | Tornier |
| 4,484,570 A | 11/1984 | Sutter et al. |
| 4,488,543 A | 12/1984 | Tornier |
| 4,493,317 A | 1/1985 | Klaue |
| 4,506,662 A | 3/1985 | Anapliotis |
| 4,565,193 A | 1/1986 | Streli |
| 4,651,724 A | 3/1987 | Berentey et al. |
| 4,712,541 A | 12/1987 | Harder et al. |
| 4,733,654 A | 3/1988 | Marino |
| 4,776,330 A | 10/1988 | Chapman et al. |
| 4,794,919 A | 1/1989 | Nilsson |
| 4,800,874 A | 1/1989 | David et al. |
| 4,867,144 A | 9/1989 | Karas et al. |
| 4,915,092 A | 4/1990 | Firica et al. |
| 4,923,471 A | 5/1990 | Morgan |
| 4,955,886 A | 9/1990 | Pawluk |
| 4,988,350 A | 1/1991 | Herzberg |
| 5,002,544 A | 3/1991 | Klaue et al. |
| 5,006,120 A | 4/1991 | Carter |
| 5,013,313 A | 5/1991 | Surer |
| 5,013,314 A | 5/1991 | Firica et al. |
| 5,015,248 A | 5/1991 | Burstein et al. |
| 5,035,697 A | 7/1991 | Frigg |
| 5,041,113 A | 8/1991 | Biedermann et al. |
| 5,057,110 A | 10/1991 | Kranz et al. |
| 5,085,660 A | 2/1992 | Lin |
| 5,108,399 A | 4/1992 | Eitenmuller et al. |
| 5,127,912 A | 7/1992 | Ray et al. |
| 5,151,103 A | 9/1992 | Tepic et al. |
| 5,190,544 A | 3/1993 | Chapman et al. |
| 5,197,966 A | 3/1993 | Sommerkamp |
| 5,201,733 A | 4/1993 | Etheredge, III |
| 5,261,910 A | 11/1993 | Warden |
| 5,275,601 A | 1/1994 | Gogolewski et al. |
| 5,304,180 A | 4/1994 | Slocum |
| 5,352,228 A | 10/1994 | Kummer et al. |
| 5,352,229 A | 10/1994 | Goble et al. |
| 5,356,253 A | 10/1994 | Whitesell |
| 5,356,410 A | 10/1994 | Pennig |
| 5,364,399 A | 11/1994 | Lowery et al. |
| 5,382,248 A | 1/1995 | Jacobson et al. |
| 5,437,667 A | 8/1995 | Papierski et al. |
| 5,443,509 A | 8/1995 | Boucher et al. |
| 5,458,654 A | 10/1995 | Tepic |
| 5,462,547 A | 10/1995 | Weigum |
| 5,472,444 A | 12/1995 | Huebner et al. |
| 5,484,438 A | 1/1996 | Pennig |
| 5,486,176 A | 1/1996 | Hildebrand et al. |
| 5,527,311 A | 6/1996 | Procter et al. |
| 5,531,745 A | 7/1996 | Ray |
| 5,531,746 A | 7/1996 | Errico et al. |
| 5,536,127 A | 7/1996 | Pennig |
| 5,549,612 A | 8/1996 | Yapp et al. |
| 5,558,674 A | 9/1996 | Heggeness et al. |
| 5,578,035 A | 11/1996 | Lin |
| 5,586,985 A | 12/1996 | Putnam et al. |
| 5,591,168 A | 1/1997 | Judet et al. |
| 5,601,553 A | 2/1997 | Trebint et al. |
| 5,603,715 A | 2/1997 | Kessler |
| 5,607,426 A | 3/1997 | Ralph et al. |
| 5,616,144 A | 4/1997 | Yapp et al. |
| 5,662,655 A | 9/1997 | Laboureau et al. |
| 5,665,086 A | 9/1997 | Itoman et al. |
| 5,665,087 A | 9/1997 | Huebner |
| 5,665,088 A | 9/1997 | Gil et al. |
| 5,665,089 A | 9/1997 | Dall et al. |
| 5,669,915 A | 9/1997 | Caspar et al. |
| 5,676,667 A | 10/1997 | Hausman |
| 5,709,682 A | 1/1998 | Medoff |
| 5,709,686 A | 1/1998 | Talos et al. |
| 5,718,705 A | 2/1998 | Sammarco |
| 5,728,099 A | 3/1998 | Tellman et al. |
| 5,733,287 A | 3/1998 | Tepic et al. |
| 5,749,872 A | 5/1998 | Kyle et al. |
| 5,766,174 A | 6/1998 | Perry |
| 5,772,662 A | 6/1998 | Chapman et al. |
| 5,776,194 A | 7/1998 | Mikol et al. |
| 5,807,396 A | 9/1998 | Raveh |
| 5,851,207 A | 12/1998 | Cesarone |
| 5,853,413 A | 12/1998 | Carter et al. |
| 5,879,350 A | 3/1999 | Sherman |
| 5,931,839 A | 8/1999 | Medoff |
| 5,935,128 A | 8/1999 | Carter et al. |
| 5,938,664 A | 8/1999 | Winquist et al. |
| 5,941,878 A | 8/1999 | Medoff |
| 5,951,557 A | 9/1999 | Luter |
| 5,954,722 A | 9/1999 | Bono |
| 5,964,763 A | 10/1999 | Incavo |
| 5,967,046 A | 10/1999 | Muller |
| 5,968,046 A | 10/1999 | Castleman |
| 5,968,047 A | 10/1999 | Reed |
| 5,989,254 A | 11/1999 | Katz |
| 6,007,535 A | 12/1999 | Rayhack et al. |
| 6,010,503 A | 1/2000 | Richelsoph |
| 6,010,505 A | 1/2000 | Asche et al. |
| 6,022,350 A | 2/2000 | Ganem |
| 6,053,917 A | 4/2000 | Sherman |
| 6,093,201 A | 7/2000 | Cooper et al. |
| 6,096,040 A | 8/2000 | Esser |
| 6,123,709 A | 9/2000 | Jones |
| 6,129,730 A | 10/2000 | Bono et al. |
| 6,146,384 A | 11/2000 | Lee et al. |
| 6,152,927 A | 11/2000 | Farris et al. |
| 6,183,475 B1 | 2/2001 | Lester et al. |
| 6,197,028 B1 | 3/2001 | Ray et al. |
| 6,206,881 B1 | 3/2001 | Frigg et al. |
| 6,221,073 B1 | 4/2001 | Weiss et al. |
| D443,060 S | 5/2001 | Benirschke et al. |
| 6,228,285 B1 | 5/2001 | Wang et al. |
| 6,231,576 B1 | 5/2001 | Frigg et al. |
| 6,235,033 B1 | 5/2001 | Brace et al. |
| 6,235,034 B1 | 5/2001 | Bray |
| 6,238,395 B1 | 5/2001 | Bonutti |
| 6,241,736 B1 | 6/2001 | Sater et al. |
| 6,248,109 B1 | 6/2001 | Stoffella |
| 6,258,089 B1 | 7/2001 | Campbell et al. |
| 6,270,499 B1 | 8/2001 | Leu et al. |
| 6,283,969 B1 | 9/2001 | Grusin et al. |
| 6,290,703 B1 | 9/2001 | Ganem |
| 6,322,562 B1 | 11/2001 | Wolter |
| 6,355,041 B1 | 3/2002 | Martin |
| 6,355,042 B2 | 3/2002 | Winquist et al. |
| 6,355,043 B1 | 3/2002 | Adam |
| 6,358,250 B1 | 3/2002 | Orbay |
| 6,364,882 B1 | 4/2002 | Orbay |
| 6,379,359 B1 | 4/2002 | Dahners |
| 6,383,186 B1 | 5/2002 | Michelson |
| 6,409,768 B1 | 6/2002 | Tepic et al. |
| 6,440,135 B2 | 8/2002 | Orbay et al. |
| 6,454,769 B2 | 9/2002 | Wagner et al. |
| 6,454,770 B1 | 9/2002 | Klaue |
| 6,458,133 B1 | 10/2002 | Lin |
| 6,468,278 B1 | 10/2002 | Muckter |
| 6,508,819 B1 | 1/2003 | Orbay |
| 6,527,775 B1 | 3/2003 | Warburton |

(56) References Cited

U.S. PATENT DOCUMENTS

| | | |
|---|---|---|
| 6,540,748 B2 | 4/2003 | Lombardo |
| 6,595,993 B2 | 7/2003 | Donno et al. |
| 6,599,290 B2 | 7/2003 | Bailey et al. |
| 6,602,255 B1 | 8/2003 | Campbell et al. |
| 6,623,486 B1 | 9/2003 | Weaver et al. |
| 6,626,908 B2 | 9/2003 | Cooper et al. |
| 6,645,212 B2 | 11/2003 | Goldhahn et al. |
| 6,652,525 B1 | 11/2003 | Assaker et al. |
| 6,669,700 B1 | 12/2003 | Farris et al. |
| 6,679,883 B2 | 1/2004 | Hawkes et al. |
| 6,692,503 B2 | 2/2004 | Foley |
| 6,706,046 B2 | 3/2004 | Orbay et al. |
| 6,712,820 B2 | 3/2004 | Orbay |
| 6,719,758 B2 | 4/2004 | Beger et al. |
| 6,719,759 B2 | 4/2004 | Wagner |
| 6,730,090 B2 | 5/2004 | Orbay et al. |
| 6,730,091 B1 | 5/2004 | Pfefferle et al. |
| 6,755,831 B2 | 6/2004 | Putnam |
| 6,761,719 B2 | 7/2004 | Justis et al. |
| 6,767,351 B2 | 7/2004 | Orbay et al. |
| 6,780,186 B2 | 8/2004 | Errico et al. |
| 6,821,278 B2 | 11/2004 | Frigg et al. |
| 6,866,665 B2 | 3/2005 | Orbay |
| 6,926,720 B2 | 8/2005 | Castaneda |
| 6,955,677 B2 | 10/2005 | Dahners |
| 6,974,461 B1 | 12/2005 | Wolter |
| 7,044,951 B2 | 5/2006 | Medoff et al. |
| 7,090,676 B2 | 8/2006 | Huebner et al. |
| 7,153,309 B2 | 12/2006 | Huebner et al. |
| 7,207,993 B1 | 4/2007 | Baldwin et al. |
| 7,857,838 B2 | 12/2010 | Orbay |
| 8,556,945 B2 | 10/2013 | Orbay |
| 2001/0001119 A1 | 5/2001 | Lombardo |
| 2001/0011172 A1 | 8/2001 | Orbay et al. |
| 2001/0021851 A1 | 9/2001 | Eberlein et al. |
| 2002/0032446 A1 | 3/2002 | Orbay |
| 2002/0049445 A1 | 4/2002 | Hall, IV et al. |
| 2002/0058939 A1 | 5/2002 | Wagner et al. |
| 2002/0058941 A1 | 5/2002 | Clark et al. |
| 2002/0111629 A1 | 8/2002 | Phillips |
| 2002/0147452 A1 | 10/2002 | Medoff et al. |
| 2002/0151899 A1 | 10/2002 | Bailey et al. |
| 2002/0156474 A1 | 10/2002 | Wack et al. |
| 2003/0045880 A1 | 3/2003 | Michelson |
| 2003/0073999 A1 | 4/2003 | Putnam |
| 2003/0078583 A1 | 4/2003 | Biedermann et al. |
| 2003/0083660 A1 | 5/2003 | Orbay |
| 2003/0083661 A1 | 5/2003 | Orbay et al. |
| 2003/0105461 A1 | 6/2003 | Putnam |
| 2003/0135212 A1 | 7/2003 | Chow |
| 2003/0153918 A1 | 8/2003 | Putnam |
| 2003/0153919 A1 | 8/2003 | Harris |
| 2003/0216735 A1 | 11/2003 | Altarac et al. |
| 2004/0030339 A1 | 2/2004 | Wack et al. |
| 2004/0059334 A1 | 3/2004 | Weaver et al. |
| 2004/0059335 A1 | 3/2004 | Weaver et al. |
| 2004/0068319 A1 | 4/2004 | Cordaro |
| 2004/0073218 A1 | 4/2004 | Dahners |
| 2004/0097934 A1 | 5/2004 | Farris et al. |
| 2004/0097937 A1 | 5/2004 | Pike et al. |
| 2004/0102778 A1 | 5/2004 | Huebner et al. |
| 2004/0111090 A1 | 6/2004 | Dahners |
| 2004/0167522 A1 | 8/2004 | Niederberger et al. |
| 2004/0193155 A1 | 9/2004 | Castaneda |
| 2004/0193163 A1 | 9/2004 | Orbay |
| 2004/0193164 A1 | 9/2004 | Orbay |
| 2004/0193165 A1 | 9/2004 | Orbay |
| 2004/0260291 A1 | 12/2004 | Jensen |
| 2005/0004574 A1 | 1/2005 | Muckter |
| 2005/0010226 A1 | 1/2005 | Grady et al. |
| 2005/0065522 A1 | 3/2005 | Orbay |
| 2005/0065523 A1 | 3/2005 | Orbay |
| 2005/0065524 A1 | 3/2005 | Orbay |
| 2005/0085818 A1 | 4/2005 | Huebner |
| 2005/0131413 A1 | 6/2005 | O'Driscoll et al. |
| 2005/0154392 A1 | 7/2005 | Medoff et al. |
| 2005/0165400 A1 | 7/2005 | Fernandez |

FOREIGN PATENT DOCUMENTS

| | | | |
|---|---|---|---|
| DE | 33 01 298 | 2/1984 | |
| DE | 40 04 941 | 8/1990 | |
| DE | 195 42 116 A | 5/1997 | |
| DE | 196 29 011 | 1/1998 | |
| DE | 93 21 544 U1 | 9/1999 | |
| DE | 43 43 117 C2 | 11/1999 | |
| EP | 0 451 427 A1 | 5/1990 | |
| EP | 0556548 A1 | 8/1993 | |
| EP | 1250892 A2 | 10/2002 | |
| WO | WO 97/47251 | 12/1997 | |
| WO | WO 99/56653 | 11/1999 | |
| WO | WO 00/04836 | 2/2000 | |
| WO | WO 00/36984 | 6/2000 | |
| WO | WO 0112081 A1 | 2/2001 | |
| WO | WO 01/19267 A1 | 3/2001 | |
| WO | WO 02/096309 | 12/2002 | |
| WO | WO 03/020007 | 3/2003 | |
| WO | WO 2004/032751 | 4/2004 | |
| WO | WO 2004/096067 | 11/2004 | |
| WO | WO 2005048857 A1 * | 6/2005 | ............ A61B 17/80 |
| WO | WO 03/101320 | 12/2013 | |

OTHER PUBLICATIONS 3.5 MM LCP Proximal Tibia Plates,Technique Guide, Synthes, 2004.
Distal Femoral Locked Plating System, POLYAX™ Wide Angle Freedom, 2005 DePuy Orthopaedics, Inc., 5M0606, 0612-54-501 (Rev.1).
Proximal Tibia Plate Instrument and Implant Set, Synthes Sep. 2000.
Synthes 2002 Catalog, pp. 2b-35, 2b-59.
"Numelock II Polyaxial Locking System," Stryker Corporation, brochure.
"SMARTLock Locking Screw Technology," Stryker Corporation, website description, 2004, www.stryker.lcom.
"Universal Distal Radius System", Stryker Corporation, website description, 2004, www.stryker.com.
"VAL PLATE (Volar Angle Locking) for Distal Radius Fractures", US Implants, brochure.
"Volar Peg Plate Insertion Technique", Trimed, Inc., brochure.
"Volar Radius Plate with Angular Stability", I.T.S. (Implant Technology Systems), 510(k) Summary of Safety and Effectiveness, Feb. 6, 2004.
"Volare Winkelstabile Radiusplatte", I.T.S. (Implant Technology Systems), Spectromed, brochure, 2005, Austria.
Moftakhar, Roham, M.D. and Trost, Gregory R., M.D., "Anterior Cervical Plates: A Historical Perspective", Jan. 2004, pp. 1-5.
Nelson, "Volar Plating with Anatomic Placement and Fixed-Angle Screws", Quick Reference Guide for Contours VPS Volar Plate System by ORTHOFIX, May 2005, www.orthofix.com.
Polyaxial and Monoaxial Spinal Screws, XIA.TM. Spinal System, www.osteonics.com/osteonics/spine/xia2.html, Jun. 25, 2002.
Osada et al, "Biomechanics in Uniazial Compression of Three Distal Radius Volar Plates", the Journal of Hand Surgery (2004).
Orbay, "Surgical Innovations; Advances in Distal Radius Fixation" (Mar./Apr. 2003).
"SCS™/D Distal Radius Plate System: Dorsal", Avanta, 1997.
"SCS™/V Distal Radius Plate: Volar", Avanta, 1998.
"The Distal Radius Plate Instrument and Implant Set", Technique Guide, Synthes®, Paoli, PA 1995.
"The Titanium Distal Radius Plate", Technique Guide, Synthes®, Paoli, PA 1995.
Advances in Distal Radius Fracture Management(D) transcript of American Academy of Orthopaedic Surgeons 2001 Conference, pp. 134-151, Feb. 28, 2001, including article by Matthew D. Putnam MD, entitled "Repair and Rehabilitation of Distal Radius Fractures: the Role of Subchondral Fixation" at pp. 144-147.
"Summary of Safety and Effectiveness Information"; Synthes; Jul. 29, 1998.

* cited by examiner

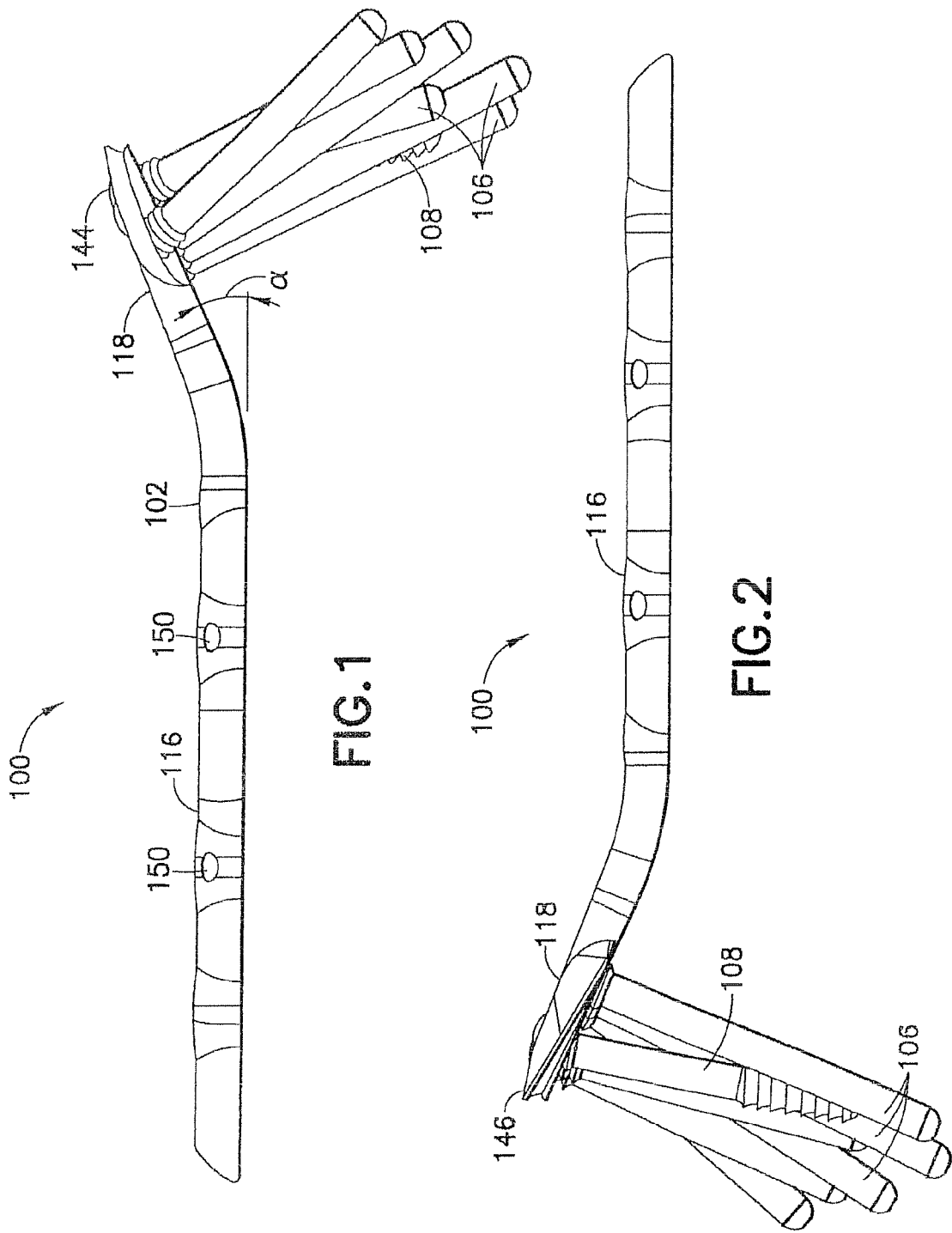

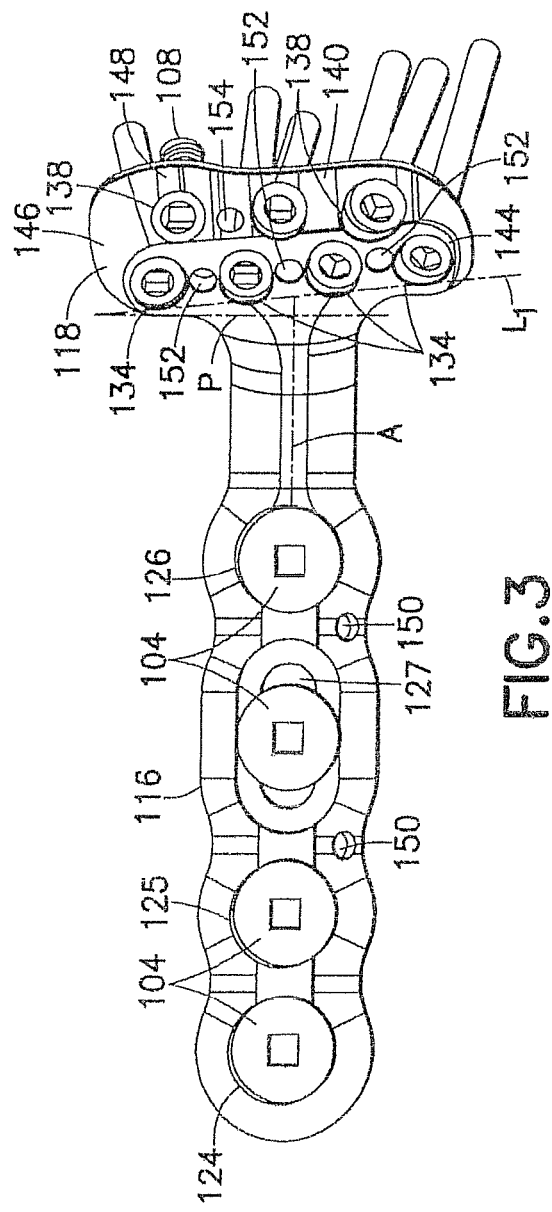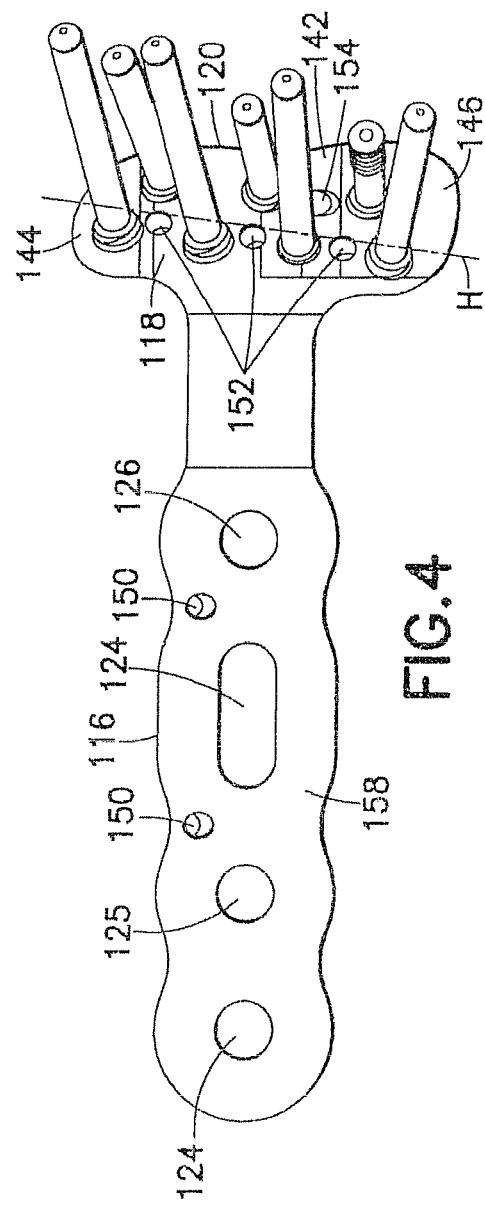

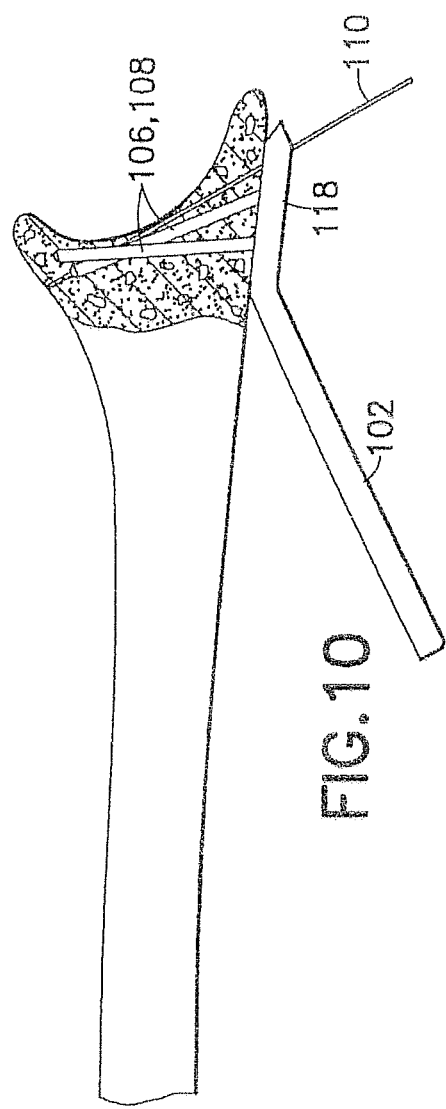
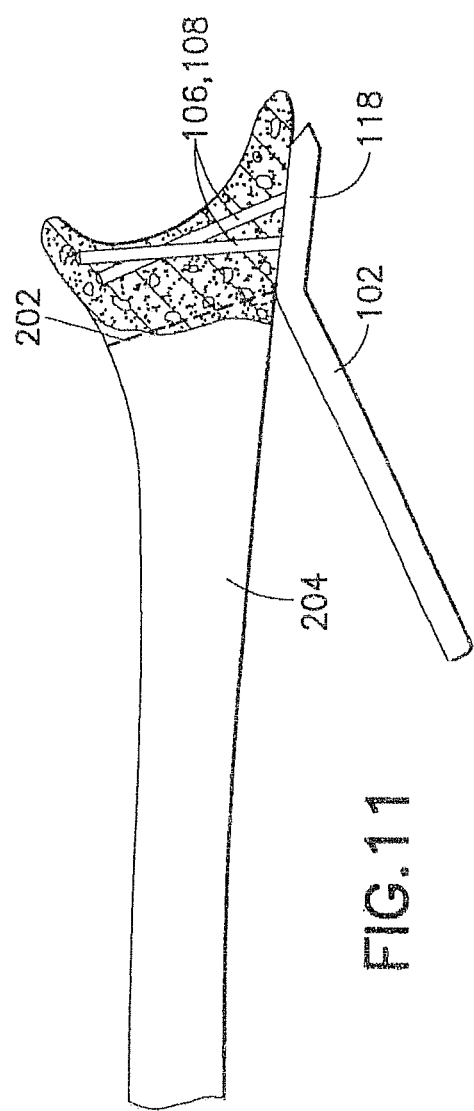

DISTAL RADIUS FRACTURE FIXATION PLATE WITH ULNAR BUTTRESS

CROSS-REFERENCE TO RELATED APPLICATIONS

This application is a continuation of U.S. Ser. No. 12/791,405, filed Jun. 1, 2010, which is a continuation of U.S. Ser. No. 10/664,371, filed Sep. 17, 2003, now issued as U.S. Pat. No. 7,857,838, which are hereby incorporated by reference herein in their entireties.

BACKGROUND OF THE INVENTION

1. Field of the Invention

This invention relates broadly to surgical implants. More particularly, this invention relates to a bone fracture fixation system for distal radius fractures.

2. State of the Art

Fracture to the metaphyseal portion of a long bone can be difficult to treat. Improper treatment can result in deformity and long-term discomfort.

By way of example, a Colles' fracture is a fracture resulting from compressive forces being placed on the distal radius, and which causes backward or dorsal displacement of the distal fragment and radial deviation of the hand at the wrist. Often, a Colles' fracture will result in multiple bone fragments which are movable and out of alignment relative to each other. If not properly treated, such fractures may result in permanent wrist deformity and limited articulation of the wrist. It is therefore important to align the fracture and fixate the bones relative to each other so that proper healing may occur.

Alignment and fixation of a metaphyseal fracture (occurring at the extremity of a shaft of a long bone) are typically performed by one of several methods: casting, external fixation, interosseous wiring, and plating. Casting is non-invasive, but may not be able to maintain alignment of the fracture where many bone fragments exist. Therefore, as an alternative, external fixators may be used. External fixators utilize a method known as ligamentotaxis, which provides distraction forces across the joint and permits the fracture to be aligned based upon the tension placed on the surrounding ligaments. However, while external fixators can maintain the position of the wrist bones, it may nevertheless be difficult in certain fractures to first provide the bones in proper alignment. In addition, external fixators are often not suitable for fractures resulting in multiple bone fragments. Interosseous wiring is an invasive procedure whereby screws are positioned into the various fragments and the screws are then wired together as bracing. This is a difficult and time-consuming procedure. Moreover, unless the bracing is quite complex, the fracture may not be properly stabilized. Plating utilizes a stabilizing metal plate typically against the dorsal side of the bones, and a set of parallel pins extending from the plate into holes drilled in the bone fragments to provide stabilized fixation of the fragments. However, many currently available plate systems fail to provide desirable alignment and stabilization.

In particular, with a distal radius fracture the complex shape of the distal radius, including the bulky volar rim of the lunate fossa, relatively flat volar rim of the scaphoid fossa, and volar marginal fragment from the lunate fossa should be accommodated. A fixation plate should provide desirable alignment and stabilization of both the subchondral bone and the articular surfaces of the distal radius.

SUMMARY OF THE INVENTION

It is therefore an object of the invention to provide an improved fixation system for distal radius fractures.

It is another object of the invention to provide a distal radius volar fixation system that desirably aligns and stabilizes multiple bone fragments in a fracture to permit proper healing.

It is also an object of the invention to provide a distal radius volar plate system which provides support for articular and subchondral surfaces.

It is an additional object of the invention to provide a distal radius volar plate system which accommodates the anatomical structure of the metaphysis of the distal radius.

It is a further object of the invention to provide a distal radius volar plate system which provides support without interfering with ligaments and soft tissues near the edge of the articular surface.

In accord with these and other objects, which will be discussed in detail below, a distal radius volar fixation system is provided. The system generally includes a plate intended to be positioned against the volar side of the radius, a plurality of bone screws for securing the plate along a non-fractured portion of the radius bone, a plurality of bone pegs sized to extend from the plate and into bone fragments at the metaphysis of a radius bone, and one or more K-wires to facilitate alignment and fixation of the plate over the bone and guide the process of application.

The plate is generally T-shaped, defining an elongate body and a generally transverse head angled upward relative to the body, and includes a first side which is intended to contact the bone, and a second side opposite the first side. The body includes a plurality of countersunk screw holes for the extension of the bone screws therethrough, and optionally one or more substantially smaller alignment holes. The lower surfaces of the radial and ulnar side portions of the head are contoured upward (in a Z direction) relative to the remainder of the head to accommodate the lunate and scaphoid processes. An extension is provided at the head portion along the distal ulnar side of the head to buttress the volar lip (marginal fragment) of the lunate fossa of the radius bone, thereby providing support to maintain the wrist within the articular socket. Moreover, the contoured shape provides a stable shape that prevents rocking of the plate on the bone. The upper and lower surfaces are chamfered to have a reduced profile that limits potential interface with the ligaments and soft tissue near the edge of the lunate fossa. The head includes a plurality of threaded peg holes for receiving the pegs therethrough. The peg holes are arranged into a first set provided in a proximal portion of the head, and a second relatively distal set preferably provided in the tapered portion of the head.

The first set of the peg holes is substantially linearly arranged generally laterally across the head. The line of pegs is preferably slightly oblique relative to a longitudinal axis through the body of the plate. Axes through the first set of holes are preferably oblique relative to each other, and are preferably angled relative to each other in two dimensions such that pegs inserted therethrough are similarly obliquely angled relative to each other. The pegs in the first set of peg holes provide support for the dorsal aspect of the subchondral bone fragments.

The second set of peg holes is provided relatively distal of the first set. The holes of the second set, if more than one are provided, are slightly out of alignment but generally linearly arranged. The pegs in the second set of peg holes provide support for the volar aspect of the subchondral bone, behind and substantially parallel to the articular bone surface.

A distal alignment hole is provided generally between two peg holes of the second set of peg holes. At the upper surface of the plate, the distal alignment hole is substantially cylindrical, while at the lower surface, the hole is laterally oblong.

One or more proximal alignment holes of a size substantially smaller than the peg holes are provided substantially along a distal edge defined by a tangent line to shafts of pegs inserted in the first set of peg holes, and facilitate temporary fixation of the plate to the bone with K-wires. Furthermore, along the body two longitudinally displaced alignment holes are also provided. All of the alignment holes are sized to closely receive individual K-wires.

The plate may be used in at least two different manners. According to a first use, the surgeon reduces a fracture and aligns the plate thereover. The surgeon then drills K-wires through the proximal alignment holes to temporarily fix the orientation of the head of the plate to the distal fragment. Once the alignment is so fixed, the fracture is examined, e.g., under fluoroscopy, to determine whether the K-wires are properly aligned relative to the articular surface. As the axes of the proximal alignment holes correspond to axes of adjacent peg holes, the fluoroscopically viewed K-wires provide an indication as to whether the pegs will be properly oriented. If the placement is correct, the K-wires maintain the position of the plate over the fracture. The peg holes may then be drilled with confidence that their locations and orientations are proper. If placement is not optimal, the K-wires can be removed and the surgeon has an opportunity to relocate and/or reorient the K-wires and drill again. Since each K-wire is of relatively small diameter, the bone is not significantly damaged by the drilling process and the surgeon is not committed to the initial drill location and/or orientation.

According to a second use, the plate may be used to correct a metaphyseal deformity (such as malformed fracture or congenital deformity). For such purposes, a K-wire is drilled into the bone parallel to the articular surface in the lateral view under fluoroscopy until one end of the K-wire is located within or through the bone and the other end is free. The free end of the K-wire is guided through the distal oblong alignment hole of the head of the plate, and the plate is slid down over the K-wire into position against the bone. The oblong alignment hole permits the plate to tilt laterally over the K-wire to sit flat on the bone, but does not permit movement of the plate over the K-wire in the anterior-posterior plane. The surgeon drills holes in the bone in alignment with the peg holes and then fixes the plate relative the bone with pegs. The bone is then cut, and the body of the plate is levered toward the shaft of the bone to re-orient the bone. The body of the plate is then fixed to the shaft to correct the anatomical defect.

Additional objects and advantages of the invention will become apparent to those skilled in the art upon reference to the detailed description taken in conjunction with the provided figures.

BRIEF DESCRIPTION OF THE DRAWINGS

FIG. 1 is a radial side elevation of a right-hand volar plate according to the invention, shown with pegs coupled thereto;

FIG. 2 is an ulnar side elevation of a right-hand volar plate according to the invention, shown with pegs coupled thereto;

FIG. 3 is top view of a right-hand volar plate according to the invention, shown with pegs and screws;

FIG. 4 is bottom view of a right-hand volar plate according to the invention, shown with pegs coupled thereto;

FIGS. 7 through 12 illustrate a method of performing an osteotomy of the distal radius according to the invention.

DETAILED DESCRIPTION OF THE PREFERRED EMBODIMENTS

Figure 5:
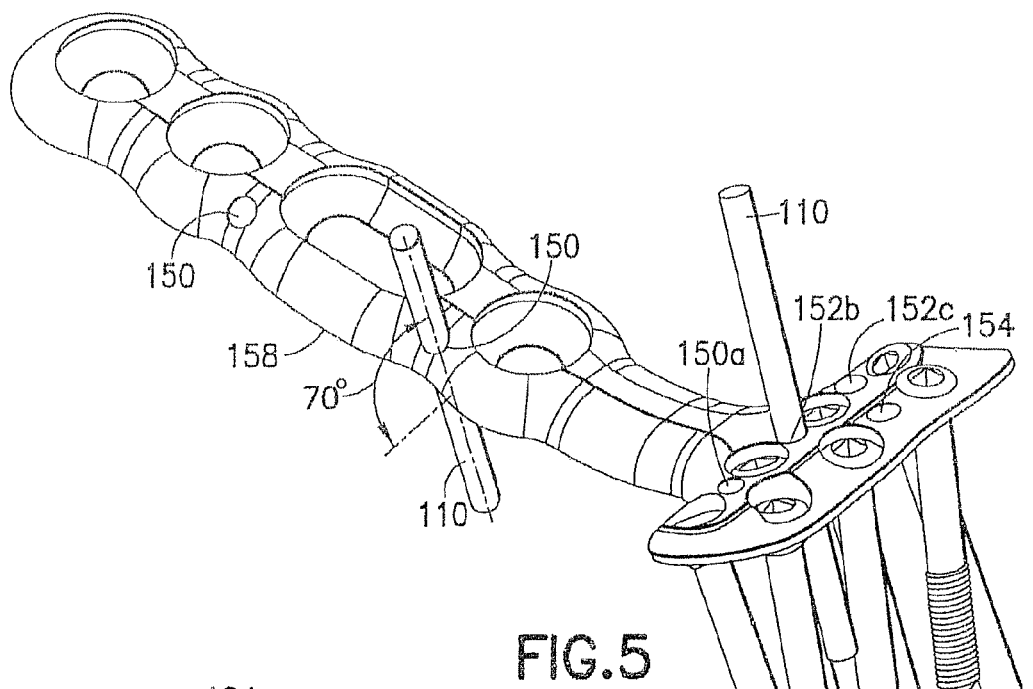
FIG. 5 is a perspective view of a right-hand volar plate according to the invention, shown with pegs coupled thereto and K-wires extending through body and proximal head alignment holes.
Figure 6:
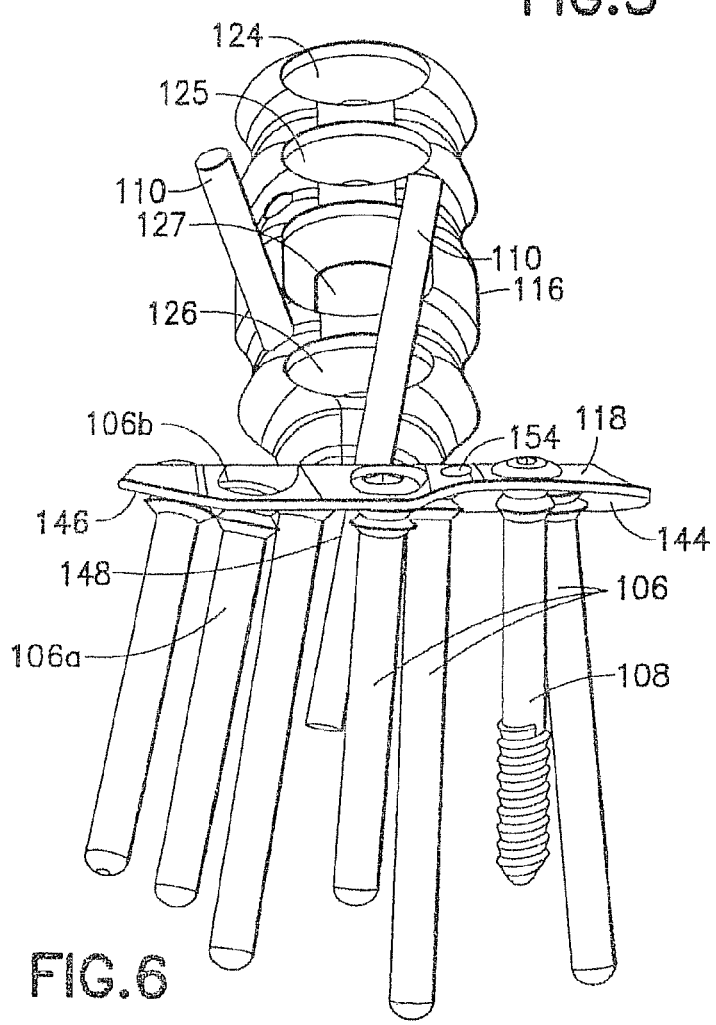
FIG. 6 is a front end view of a right-hand volar plate according to the invention, shown with pegs coupled thereto and K-wires extending through alignment holes.

Turning now to FIGS. 1 through 6, a fracture fixation system 100 according to the invention is shown. The system 100 is particularly adapted for aligning and stabilizing multiple bone fragments in a dorsally displaced distal radius fracture (or Colles' fracture). The system 100 generally includes a substantially rigid T-shaped plate 102, commonly called a volar plate, bone screws 104 (FIG. 3), pegs 106, 108, and K-wires 110 (FIGS. 5 and 6). Pegs 106 have a threaded head and a non-threaded shaft, and pegs 108 have both a threaded head and a threaded shaft. Either pegs 106 or 108, or a combination thereof may be used at the discretion of the surgeon. Exemplar pegs are described in more detail in U.S. Pat. No. 6,364,882, which is hereby incorporated by reference herein in its entirety.

The volar plate 102 shown in the figures is a right-hand plate intended to be positioned against the volar side of a fractured radius bone of the right arm. It is appreciated that a left-hand volar plate is substantially a mirror image of the plate shown and now described. The T-shaped plate 102 defines an elongate body 116, and a head 118 angled upward (in the Z-direction) relative to the head. The angle α a between the head 118 and the body 116 is preferably approximately 25°. The head 118 includes a distal buttress 120 (i.e., the portion of the head distal a first set of peg holes 134, discussed below). The plate 102 has a thickness of preferably approximately 0.1 inch, and is preferably made from a titanium alloy, such as Ti-6Al-4V.

Referring to FIG. 4, the body 116 includes four preferably countersunk screw holes 124, 125, 126, 127 for the extension of bone screws 104 therethrough (FIG. 2). One of the screw holes, 127, is preferably generally oval in shape permitting longitudinal movement of the plate 102 relative to the shaft of a bone screw when the screw is not tightly clamped against the plate.

Referring to FIGS. 3 and 4, according to one preferred aspect of the plate 102, the head portion 118 includes a first set of threaded peg holes 134 (for placement of pegs 106 and/or 108 therein) and a second set of threaded peg holes 138 (for placement of pegs 106 and/or 108 therein). The peg holes 134 of the first set are arranged substantially parallel to a line $L_1$ that is preferably slightly skewed (e.g., by 5°-10°) relative to a perpendicular P to the axis A of the body portion 116. Axes through the first set of peg holes (indicated by the pegs 106 extending therethrough) are preferably oblique relative to each other, and are preferably angled relative to each other in two dimensions, generally as described in commonly-owned U.S. Pat. No. 6,364,882, which is hereby incorporated by reference herein in its entirety. This orientation of the pegs operates to stabilize and secure the head 118 of the plate 102 on the bone even where such pegs 106 do not have threaded shafts.

The second set of peg holes 138 is provided relatively distal of the first set of peg holes 134 and is most preferably primarily located in the buttress 120. Each of the peg holes 138 preferably defines an axis that is oblique relative to the other of peg holes 136 and 138. Thus, each and every peg 106, 108 when positioned within respective peg holes 134, 138 defines a distinct axis relative to the other pegs. Moreover, the axes of the peg holes 138 are preferably oriented relative to the axes of peg holes 134 such that pegs 106, 108 within peg holes 138 extend (or define axes which extend) between pegs (or axes thereof) within peg holes 134 in an interleaved manner.

Referring specifically to FIGS. 1, 2, 5 and 6, according to another preferred aspect of the plate 102, in order to approximate the anatomy for ideal fracture support and maintain a low profile, the upper and lower surfaces 140, 142, respectively of the buttress 120 are chamfered, with the chamfer of the lower surface 142 being contoured for the anatomical structure that it will overlie. In particular, the lower surface 142 at an ulnar-side portion 144 of the head portion 118 is contoured upward (in a Z direction) both distally and laterally to accommodate the bulky volar rim of the lunate fossa, and the lower surface 142 at a radial side portion 146 of the head 118 is contoured upward laterally relative to the remainder of the head to accommodate a prominence at the radial aspect of the bone, as indicated by the visibility of these lower surfaces in the side views of FIGS. 1 and 2 and head-on view of FIG. 6. The contoured shape (with generally three defined planes) provides a stable shape that prevents rocking of the plate on the bone. In addition, the upper and lower surfaces 140, 142 are chamfered to have a reduced profile that limits potential interface with the ligaments and soft tissue near the edge of the articular surface. A distal extension 148 is also provided at the ulnar side portion 146 to further buttress the volar lip (volar marginal fragment of the lunate fossa) of the articular socket of the radius bone, thereby providing support to maintain the wrist within the articular socket.

Referring specifically to FIGS. 3 and 4, according to a further preferred aspect of the invention, the plate 102 is provided with body alignment holes 150, proximal head alignment holes 152a, 152b, 152c (generally 152), and a distal head alignment hole 154, each sized to closely accept standard Kirschner wires (K-wires), e.g., 0.7-1.2 mm in diameter. All the alignment holes 150, 152, 154 are substantially smaller in diameter (e.g., by thirty to fifty percent) than the shafts of screws 104 (approximately 3.15 mm in diameter) and the shafts of pegs 106, 108 (approximately 2.25 mm in diameter). The body alignment holes 150 are longitudinally displaced along the body portion 116 and provided at an oblique angle (preferably approximately 70°, as shown in FIG. 5) relative to the lower surface 158 of the body portion 116. The proximal head alignment holes 152 alternate with the peg holes 134. A tangent line H to the distalmost points of the head alignment holes 152 is preferably substantially coincident or closely parallel with a line tangent to points on the circumferences of the shafts of pegs 106 inserted through holes 134 adjacent the head portion 118 of the plate 102. With respect to the proximal head alignment holes, it is appreciated that a shaft 106a of a peg is generally smaller in diameter than a head 106b of a peg (FIG. 6). Thus, a line tangent to the peg holes 134 (each sized for receiving the head 106b of peg 106) will be closely located, but parallel, to a line tangent to a distalmost point on the respective alignment hole 152. Nevertheless, for purposes of the claims, both (i) a tangent line which is preferably substantially coincident with a line tangent to points on the circumferences of the shafts of pegs and (ii) a tangent line to a set of peg holes shall be considered to be "substantially coincident" with a line tangent to a distalmost point of an alignment hole 152. Axes through alignment holes 152 preferably generally approximate (within, e.g., 3°) the angle of an axis of an adjacent peg hole 134. Distal head alignment hole 154 is provided between the central and radial-side peg holes 138, and has a circular upper opening, and a laterally oblong lower opening, as shown best in FIG. 6.

The plate may be used in at least two different applications: fracture fixation and correction of a metaphyseal deformity. In either application, an incision is first made over the distal radius, and the pronator quadratus is reflected from its radial insertion exposing the entire distal radius ulnarly to the distal radioulnar joint. For fracture fixation, the surgeon reduces the fracture and aligns the plate 102 thereover. The surgeon then drills preferably two K-wires 110 through respective body alignment holes 150, and one or more K-wires through selected proximal head alignment holes 152 at the location at which the surgeon believes the pegs 106, 108 should be placed based on anatomical landmarks and/or fluoroscopic guidance. The K-wires temporarily fix the orientation of the plate to the distal fragment. While the fixation is temporary, it is relatively secure in view of the fact that the body alignment holes 150, proximal head alignment holes 152, and K-wires 110 therethrough are angled in different orientations relative to the lower surface of the plate. Once the alignment is so fixed, the fracture is examined, e.g., under fluoroscopy, to determine whether the K-wires 110 are properly aligned relative to the articular surface. As the axes of the proximal head alignment holes 152 correspond to axes of the adjacent peg holes 134, the fluoroscopically viewed K-wires 110 provide an indication as to whether the pegs 106, 108 will be properly oriented. If the placement is correct, the K-wires 110 maintain the position of the plate 102 over the fracture while holes in the bone are drilled through the screw holes 124, 125, 126, 127 for the screws 104 and peg holes 134, 138 for pegs 106, 108, with confidence that the locations and orientation of the screws and pegs inserted therein are anatomically appropriate. The K-wires can then be removed.

If fluoroscopic examination indicates that placement of the K-wires 110 is not optimal, the K-wires can be removed and the surgeon has an opportunity to relocate and/or reorient the K-wires and drill again. Since each K-wire is of relatively small diameter, the bone is not significantly damaged by the drilling process and the surgeon is not committed to the initial drill location and/or orientation.

The pegs 106 within peg holes 138 define projections that provide support at the volar aspect behind the articular surface of the bone surface. The sets of pegs 106, 108 through peg holes 134, 138 preferably laterally alternate to provide tangential cradling of the subchondral bone. A preferred degree of subchondral support is provided with four peg holes 134 (and associated pegs) through the proximal portion of the head 118 of the plate, and three peg holes 138 (and associated pegs) through the distal portion of the head 118. The fracture fixation system thereby defines a framework which substantially tangentially supports the bone fragments in their proper orientation. In accord with an alternate less preferred embodiment, suitable support may also be provided where the pegs 106 and 108 are parallel to each other or in another relative orientation or with fewer peg holes and/or pegs.

Figure 7:
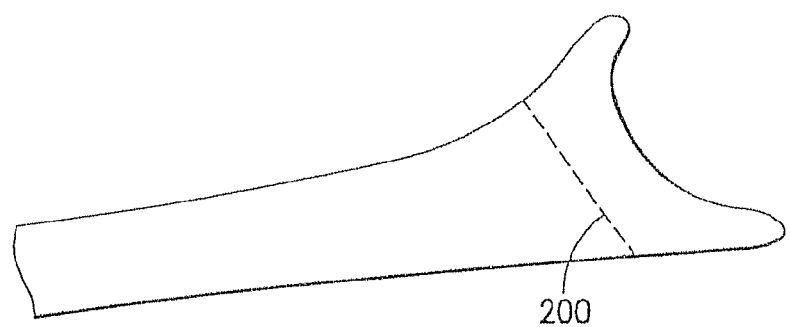
Figure 8:
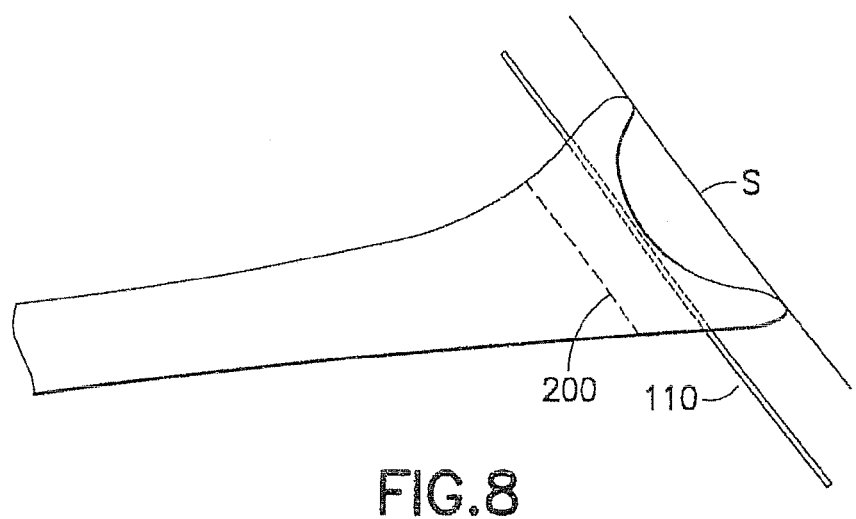
Figure 9:
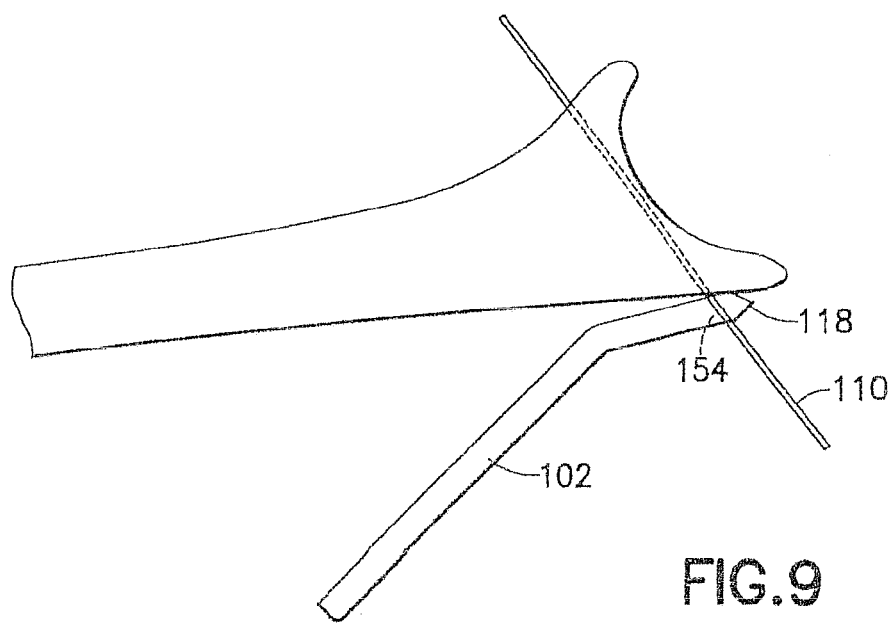
Figure 12:
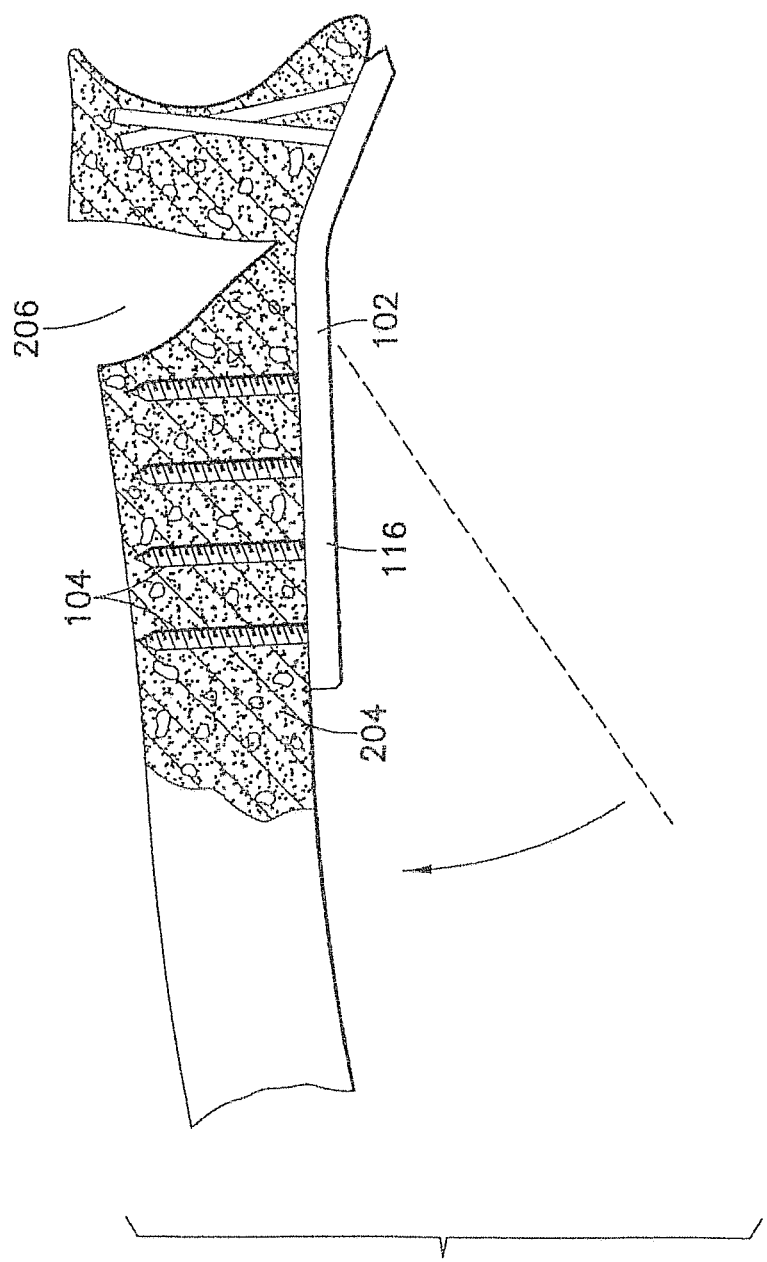

According to a second use, the plate may be used to correct a metaphyseal deformity 200 (such as malformed fracture or congenital deformity), as shown in FIG. 7. For such purposes, a K-wire 110 is drilled into the bone parallel to the articular surface S in the lateral view under fluoroscopy (FIG. 8). The free end of the K-wire 110 is guided through the oblong distal head alignment hole 154, and the plate 102 is slid down over the K-wire into position against the bone (FIG. 9). The oblong alignment hole 154 permits the plate 102 to tilt laterally over the K-wire 110 to sit flat on the bone, but does not permit tilting of plate relative to the K-wire in the anterior-posterior plane. Once the plate 102 is seated against the bone, the surgeon drills holes in the bone in alignment with the peg holes 134, 138 (FIG. 3) and then fixes the plate relative the bone with pegs 106, 108 (FIG. 10). The K-wire 110 is removed. The bone is then saw cut at 202 proximal the location of the head 118 of the plate 102 (FIG. 11), and the body 116 of the plate is levered toward the proximal diaphyseal bone 204, creating an open wedge 206 at the deformity (FIG. 12). When the body 116 of the plate 102 is in contact and longitudinal alignment with the diaphysis of the bone, the bone distal of the cut has been repositioned into the anatomically correct orientation relative to the shaft of the bone. The body 116 of the plate 102 is then secured to the bone with screws 104. Post-operatively, the open wedge in the bone heals resulting in an anatomically correct distal radius.

While fixed single-angle pegs have been disclosed for use with the plate (i.e., the pegs may be fixed in respective threaded peg holes 134, 136 only coaxial with an axis defined by the respective peg holes), it is appreciated that an articulating peg system, such as that disclosed in co-owned U.S. Pat. No. 6,440,135 or co-owned and co-pending U.S. Ser. No. 10/159,612, both of which are hereby incorporated by reference herein in their entireties, may also be used. In such articulating peg systems, the peg holes and pegs are structurally adapted such that individual pegs may be fixed at any angle within a range of angles. In addition, while less preferable, one or both sets of the pegs may be replaced by preferably blunt tines which are integrated into the plate such that the plate and tines are unitary in construct. Similarly, other elongate projections may be coupled to the plate to define the desired support.

There have been described and illustrated herein embodiments of a fixation plate, and particularly plates for fixation of distal radius fractures, as well as a method of aligning and stabilizing a distal radius fracture and performing an osteotomy. While particular embodiments of the invention have been described, it is not intended that the invention be limited thereto, as it is intended that the invention be as broad in scope as the art will allow and that the specification be read likewise. Thus, while particular materials, dimensions, and relative angles for particular elements of the system have been disclosed, it will be appreciated that other materials, dimensions, and relative angles may be used as well. In addition, while a particular number of screw holes in the volar plate and bone screws have been described, it will be understood another number of screw holes and screws may be provided. Further, fewer screws than the number of screw holes may be used to secure to the plate to the bone. Also, fewer or more peg holes and bone pegs may be used, preferably such that at least two pegs angled in two dimensions relative to each other are provided. In addition, while a particular preferred angle between the head and body has been disclosed, other angles can also be used. It will therefore be appreciated by those skilled in the art that yet other modifications could be made to the provided invention without deviating from its spirit and scope.

What is claimed is:

1. A fixation plate for fixation of a fracture at the distal radius, the distal radius having a volar surface, a dorsal surface, an ulnar side closer to an ulna, and a radial side opposite the ulnar side, the distal radius bone having a lunate fossa with a volar lip, said fixation plate for use with a plurality of fasteners that each have a fastener head portion at which the fasteners are coupled to said plate and a fastener shaft portion that can extend into the distal radius, said fixation plate comprising:

a substantially rigid plate sized to accommodate the anatomy of the volar surface of the distal radius, said plate having a proximally extending body portion and a head portion having a width greater than a width of said body portion, each of said body and head portions having a bone contacting surface, and when said bone contacting surface of said body portion is positioned on a horizontal plate, said head portion is angled upward with respect to said plane, said plate defining a first set of holes for receiving the fasteners in said head portion of said plate, and a second set of holes for receiving the fasteners in said body portion, said head portion having a radial side for placement on the volar surface at the radial side of the distal radius, and an ulnar side for placement on the volar surface at the ulnar side of the distal radius, wherein when said head portion is positioned on the volar surface of the distal radius, said head portion extends distally a greater distance on said ulnar side of said head portion than on said radial side of said head portion to support the volar lip of the lunate fossa of the distal radius.

2. A fixation plate according to claim 1, wherein:

said head portion includes a distal extension on said ulnar side to buttress the volar lip of the lunate fossa, and said first set of holes are located proximal of said distal extension.

3. A fixation plate according to claim 1, wherein:

said distal extension tapers to a non-linear distal edge.

4. A fixation plate according to claim 1, wherein:

each hole of said first set of holes includes a threaded portion.

5. A fixation plate according to claim 1, wherein:

said first set of holes includes at least four holes.

6. A fixation plate according to claim 1, wherein:

said first set of holes are structurally adapted to allow each of the fasteners to be constrained in a fixed angle relationship relative to said plate.

7. A fixation plate according to claim 6, wherein:

said plurality of holes are threaded.

8. A fixation plate according to claim 1, wherein:

said bone contacting surface of said head portion is contoured to define three planes of contact against the volar surface of the distal radius.

9. A fixation plate for fixation of a fracture at the distal radius, the distal radius having a volar surface, a dorsal surface, an ulnar side closer to an ulna, and a radial side opposite the ulnar side, the distal radius bone having a lunate fossa with a volar lip, said fixation plate for use with a plurality of fasteners, said fixation plate comprising:

a substantially rigid plate sized to accommodate the anatomy of the volar surface of the distal radius, said plate having a proximally extending body portion and a head portion oriented at one end of the body portion and having a width greater than a width of said body portion, each of said body portion and head portion having a bone contacting surface, and when said bone contacting surface of said body portion is positioned on a horizontal plate, said head portion is angled upward with respect to said plane, said plate defining a plurality of holes for receiving the fasteners, said head portion including a radial side for placement on the volar surface at the radial side of the distal radius, and an ulnar side for placement on the volar surface at the ulnar side of the distal radius, said ulnar side having a buttress portion, wherein when said head portion is positioned on the volar surface of the distal radius said buttress portion extends distally a greater distance on said ulnar side than said radial side of said plate extends along the radial side of the radius bone, such that said plate provides support to the volar lip of the lunate fossa of the distal radius.

10. A fixation plate according to claim 9, wherein:
said head portion includes a central portion situated between said ulnar side and said radial side,
said bone contacting surface of said head portion at said ulnar side is elevated upward relative to said bone contacting surface at said central portion, and
said bone contacting surface of said head portion at said radial side is elevated upward relative to said bone contacting surface at said central portion.

11. A fixation plate according to claim 9, wherein:
said buttress portion includes at least one hole of a second set of holes.

12. A fixation plate according to claim 9, wherein:
said head portion tapers toward a distal edge.

13. A fixation plate according to claim 9, wherein:
said buttress portion tapers in thickness in a distal direction.

14. A fixation plate according to claim 9, wherein:
a first set of said plurality of holes extends in a generally medial-lateral direction.

15. A fixation plate according to claim 14, wherein:
said buttress portion is located distal of said first set of holes.

16. A fixation plate according to claim 9, wherein:
said plurality of holes are structurally adapted to allow each of the fasteners to be constrained in a fixed angle relationship relative to said plate.

17. A fixation plate according to claim 16, wherein:
said plurality of holes are threaded.

18. A fixation plate according to claim 9, wherein:
said bone contacting surface of said head portion is contoured to define three planes of contact against the volar surface of the distal radius.

* * * * *